(12) United States Patent
Ding et al.

(10) Patent No.: US 10,188,584 B2
(45) Date of Patent: Jan. 29, 2019

(54) MEDICINAL XIDING VIAL AND DISPENSING APPARATUS AND INJECTION APPARATUS THEREOF

(71) Applicants: Yiling Ding, Shaanxi (CN); Xi Ding, Shaanxi (CN)

(72) Inventors: Yiling Ding, Shaanxi (CN); Xi Ding, Shaanxi (CN)

( * ) Notice: Subject to any disclaimer, the term of this patent is extended or adjusted under 35 U.S.C. 154(b) by 90 days.

(21) Appl. No.: 14/765,310

(22) PCT Filed: Jan. 25, 2014

(86) PCT No.: PCT/CN2014/071442
§ 371 (c)(1),
(2) Date: Jul. 31, 2015

(87) PCT Pub. No.: WO2014/117691
PCT Pub. Date: Aug. 7, 2014

(65) Prior Publication Data
US 2015/0359710 A1    Dec. 17, 2015

(30) Foreign Application Priority Data

Jan. 31, 2013   (CN) .......................... 2013 1 0039075
Oct. 10, 2013   (CN) .......................... 2013 1 0471655

(51) Int. Cl.
*A61J 1/20*      (2006.01)
*A61M 5/24*     (2006.01)
(Continued)

(52) U.S. Cl.
CPC ........... *A61J 1/2013* (2015.05); *A61J 1/2096* (2013.01); *A61M 5/2429* (2013.01);
(Continued)

(58) Field of Classification Search
CPC .......... A61J 1/2003; A61J 1/20; A61J 1/2013; A61J 1/202; A61J 1/2096; A61J 1/1412;
(Continued)

(56) References Cited

U.S. PATENT DOCUMENTS 2,789,559 A *   4/1957   Breitenbach ............ A61M 5/24
                                                              134/58 R
3,368,557 A     2/1968   Vagn Hassing et al.
(Continued)

FOREIGN PATENT DOCUMENTS

CN            1586649 A      3/2005
CN          200951241 Y      9/2007
(Continued)

*Primary Examiner* — Bradley J Osinski
*Assistant Examiner* — Nilay Shah
(74) *Attorney, Agent, or Firm* — Novick, Kim & Lee, PLLC; Sang Ho Lee (57) ABSTRACT

A medicinal xiding vial, and a dispensing apparatus and an injection apparatus thereof, comprise a reversely pressed medicinal xiding vial, a reversely pressed dispensing apparatus and a reversely pressed injection apparatus thereof, a general medicinal xiding vial, and a general injection apparatus. The reversely pressed medicinal xiding vial comprises a vial body whose inner wall is a straight cylinder. A first piston is disposed on a position close to the vial opening of the vial body. A blind hole is disposed at the center of an outer bottom surface of the first piston. The vial opening is provided with an outer edge, and a seal cap is fixed on the out edge to prevent the first piston from falling off. In combination with the dispensing apparatus and the injection apparatus thereof, the medicinal xiding vial can solve the problem of secondary pollution during medicine dispensing and injection.

16 Claims, 7 Drawing Sheets

(51) Int. Cl.
*A61M 5/315* (2006.01)
*A61J 1/14* (2006.01)

(52) U.S. Cl.
CPC ...... *A61M 5/2448* (2013.01); *A61M 5/31511* (2013.01); *A61J 1/1412* (2013.01); *A61J 1/1425* (2015.05); *A61J 1/20* (2013.01); *A61J 1/201* (2015.05); *A61J 1/2003* (2015.05)

(58) Field of Classification Search
CPC .......... A61J 1/1425; A61J 1/2089; A61J 1/14; A61M 5/2425; A61M 5/2429; A61M 5/2448; A61M 5/2455; A61M 2005/2462; A61M 5/285; A61M 2005/287; A61M 5/31511; A61M 5/3515
See application file for complete search history.

(56) References Cited

U.S. PATENT DOCUMENTS

| | | | | |
|---|---|---|---|---|
| 3,739,780 | A | * | 6/1973 | Ogle .................. A61M 5/2429 604/203 |
| 3,766,919 | A | * | 10/1973 | Cloyd ................. A61M 5/2429 604/203 |
| 3,901,402 | A | * | 8/1975 | Ayres ................ A61B 5/15003 210/516 |
| 3,923,059 | A | * | 12/1975 | Ogle .................... A61J 1/2089 604/231 |
| 4,196,732 | A | * | 4/1980 | Wardlaw .............. A61J 1/2096 141/2 |
| 4,713,062 | A | | 12/1987 | Stevanato |
| 5,429,614 | A | * | 7/1995 | Fowles ................. A61J 1/2089 604/201 |
| 5,713,872 | A | * | 2/1998 | Feuerborn .......... A61M 5/3275 604/192 |
| 6,423,037 | B1 | * | 7/2002 | Hijikata ............... A61M 5/178 604/187 |
| 2002/0010995 | A1 | * | 1/2002 | Thibault ............. A61J 1/1406 29/511 |
| 2005/0245880 | A1 | * | 11/2005 | Howlett ............... A61M 5/284 604/231 |
| 2010/0204659 | A1 | | 8/2010 | Bochenko et al. |
| 2013/0018311 | A1 | | 1/2013 | Denning et al. |

FOREIGN PATENT DOCUMENTS

| | | | |
|---|---|---|---|
| CN | 201263820 Y | | 7/2009 |
| CN | 202078536 U | | 12/2011 |
| CN | 202568873 U | | 12/2012 |
| CN | 203107865 U | | 8/2013 |
| CN | 203107875 U | | 8/2013 |
| CN | 203235024 U | | 10/2013 |
| CN | 203436630 U | | 2/2014 |
| CN | 203436632 U | | 2/2014 |
| EP | 2436411 A1 | | 4/2012 |
| GB | 776404 A | * | 6/1957 ............ A61J 1/2089 |
| WO | 2004/043514 A2 | | 5/2004 |

* cited by examiner

FIG.17

MEDICINAL XIDING VIAL AND DISPENSING APPARATUS AND INJECTION APPARATUS THEREOF

TECHNICAL FIELD

The present application relates to the medical instrumentation field, more particularly, relates to a medicinal Xiding vial and a dispensing apparatus and an injection apparatus thereof.

BACKGROUND ART

As we all know, general medicinal vials include an ampoule vial, a cillin vial, a card vial and a prefilled injector, etc.

Ampoule vial is a glass vial sealed with flame and is often used to store medicines for injection, vaccines and blood serum, etc., whose cleaning, drying, sterilization and filling technologies are mature, the sealing of the filling is adopted by heating the neck of the ampoule vial that has been filled with medicinal liquid using flame, and after melting, the ampoule vial is sealed using a wire-drawing sealing process. But the ampoule vial is not applicable to non-heat resistance medicine because the sealing thereof is heated using flame; in another hand, there is a risk of affecting quality of the medicine by a medicinal liquid chemical reaction caused due to high temperature during a filling process. When an amouple vial is to be used, a grinding wheel is used to cut the vial neck, the ampoule vial neck needs to be broken off with bare hands or opened by hard substance, and medicine inside the ampoule vial is sucked using an injector for injecting, and the injector directly contacts the medicine. It is extremely easy to result in debris of the grinding wheel adhesive to the vial wall and glass debris falling into the medicinal vial during a dispensing operation process, the poisonous medicinal liquid directly contacting the skin of the dispensed person causes infection, and the medicine contacts ambient air during opening the ampoule vial, there is a problem of secondary pollution, and the dosage of the manufactured product thereof is limited.

Cillin vial was named for holding penicillin in the earlier days, while cillin vial is also called as an injector vial made of sodium calcium glass, which is a small vial with a rubber plug sealing. There are brown and transparent cillin vials, etc., which are generally made of glass. Its neck part is thinner, and the part below the vial neck has the same width. The vial opening is slightly thicker than the vial neck and is slightly thinner than the vial body. The cillin vial may be used as an iodine vial, an injection liquid vial and an oral liquid vial, etc. When the cillin vial is used as an injection liquid vial, it is similar to the ampoule vial. That is, the dispensing operation process is tedious, an injector needs to be used to suck the medicine inside the cillin vial for injection, since it is difficult to suck out the medicinal liquid due to negative pressure generated inside the vial during sucking the medicine inside the cillin vial with an injector, the sucking intensity needs to increase to allow negative pressure to be generated inside the needle tube and the medicinal liquid to be sucked into the needle tube when the vial is standing upside down, however, which results in sucking air into the needle tube at an instant of pulling out the needle tube, there is a problem of secondary pollution.

An opening of the card vial is filled with rubber plug and sealed with an aluminum cap, and a tail part thereof is sealed by a rubber piston, similar to a glass needle tube injector with prefilled medicinal liquid, and a bi-pass guide needle head and a push rod for injection are additionally configured. The guide needle head is inserted into the rubber plug of the vial opening, the push rod is placed on the rubber piston of the vial tail part for applying force during the use of the card vial, and the medicinal liquid is injected into the human body under the pressure of the piston. Since the piston is not sealed with the aluminum cap by means of pressure, the medicinal liquid is expanded during high temperature sterilization, which easily causes the piston to fall off. Thus, the card vial belongs to a product without terminal sterilization. The medicinal liquid does not contact any member of the injector during the use of the card vial, which solves the problem of secondary pollution during the injection. However, since the card vial is not a terminal sterilized product, the tail part thereof is sealed by a rubber piston which is slidable during the use, thereby requiring a high sealing reliability technology and a large manufacture cost, and the selection of the manufacture dosage type is limited.

Prefilled injector directly fills an injection medicine into a glass injector, and an injection needle head is installed on the glass injector, the injector and the medicinal liquid package container are integrated. The injection is performed directly during the use, which is greatly convenient and its quality guarantee period is same long as those of the ampoule vial and the cillin vial. There are some prominent advantages as follows: (1) there is no cross infection during the use, unclean air in a ward cannot contact the medicine, thereby achieving safety injection; (2) it is extremely convenient for doctors and nurses, and there is no need to suck medicine and install a needle head, injection are directly performed and one-time used; (3) medicine is sufficiently utilized without residual medicinal liquid; and (4) self injection is applicable to an open country. However, the prefilled injector is similarly applicable to a non-terminal sterilization product only, such as a biological activity of vaccine, etc., and the package materials thereof are expensive, which is difficult to be promoted.

For most medicines, the manufacture package thereof in a pharmaceutical factory, storage and transportation thereof during the sale and the use thereof in a hospital do not have notable variation, especially the package of the medicine decides the use pattern in a hospital, and the involved dispensing widely has a problem of secondary pollution, there is no an ideal solution all over the world, and seamless connection among medicine manufacture, sale, dispensing and injection of human body cannot be realized.

SUMMARY

1. One of the purposes of the present disclosure aims to provide an assembly comprising a reversely pressed medicinal xiding xiding vial, a reversely pressed dispensing apparatus and a reversely pressed injection apparatus, which can ensure the sealing reliability and terminal sterilization of a reversely pressed medicinal xiding vial, conveniently dispense and solve the problem of secondary pollution during the injection, thereby realizing seamless connection among medicine manufacture, sale, dispensing and injection for human body.

In order to achieve the above purpose, the following first group of technical solutions is adopted by the present disclosure.

(1.1) An assembly of a reversely pressed medicinal xiding vial and a reversely pressed injection apparatus, characterized in that it includes a reversely pressed medicinal xiding vial and a reversely pressed injection apparatus;

the reversely pressed medicinal xiding vial includes a vial body whose inner wall is a straight cylinder, a first piston is disposed on a position close to the vial opening of the vial body, a blind hole is disposed at the center of an outer bottom surface of the first piston, the vial opening is provided with an outer edge, and a seal cap is fixed on the out edge to prevent the first piston from falling off;

the reversely pressed injection apparatus includes an injection tube, a fixed push rod positioned inside the injection tube and an inner needle longitudinally penetrating the fixed push rod are disposed at the bottom center of the injection tube, a needle head of the inner needle sticks out of the fixed push rod, an outer needle is disposed at an outlet port of the injection tube, and a tail part of the outer needle is connected with a tail part of the inner needle; an inner wall of the injection tube clearance-fits an outer edge of the vial opening; and a free end of the fixed push rod is fit-connected with a blind hole at the center of an outer bottom surface of the first piston.

The further improvement of the above technical solution lies in:

an annular sealing gasket that is integrated therewith is disposed at an outer bottom surface of the first piston, the annular sealing gasket is positioned between the vial opening and the seal cap; and a free end of the fixed push rod is sleeved with an annular blade for cutting to separate the first piston and the annular sealing gasket.

The fit-connection between a free end of the fixed push rod and a blind hole at the center of an outer bottom surface of the first piston is a screw-thread connection.

The inner needle and the outer needle are integrated double-ended needle.

A pull tab is disposed at the center of the seal cap corresponding to an outer bottom surface of the first piston.

(1.2) An assembly of a reversely pressed medicinal xiding vial, a reversely pressed dispensing apparatus thereof and a reversely pressed injection apparatus, characterized in that it includes a reversely pressed medicinal xiding vial, a reversely pressed dispensing apparatus and a reversely pressed injection apparatus;

the reversely pressed medicinal xiding vial includes a vial body whose inner wall is a straight cylinder, a first piston is disposed on a position close to the vial opening of the vial body, a blind hole is disposed at the center of an outer bottom surface of the first piston, the vial opening is provided with an outer edge, and a seal cap is fixed on the out edge to prevent the first piston from falling off; a second piston is provided in the middle of the vial body a push plate is clad in the second piston, and a needle guide hole is disposed at the center of the push plate;

the reversely pressed dispensing apparatus includes a dispensing tube, a hollow needle positioned inside the dispensing tube is disposed at the bottom center of the dispensing tube; and the hollow needle is composed of a head part and a rod part; the diameter of the head part of the hollow needle is less than the diameter of the needle guide hole, and the diameter of the rod part is larger than the diameter of the needle guide hole; the head part of the hollow needle is provided with an inlet, and a side wall of the rod part is provided with an outlet; an inner wall of the dispensing tube clearance-fits an outer edge of the vial opening;

the reversely pressed injection apparatus includes an injection tube, a fixed push rod and an inner needle longitudinally penetrating the fixed push rod are disposed at the bottom center of the injection tube inside the injection tube, a needle head of the inner needle sticks out of the fixed push rod, an outer needle is disposed at an outlet port of the injection tube, and a tail part of the outer needle is connected with a tail part of the inner needle; an inner wall of the injection tube clearance-fits an outer edge of the vial opening; and a free end of the fixed push rod is fit-connected with a blind hole at the center of an outer bottom surface of the first piston.

The further improvement of the above technical solution lies in:

an annular sealing gasket that is integrated therewith is disposed at an outer bottom surface of the first piston, the annular sealing gasket is positioned between the vial opening and the seal cap; and a free end of the fixed push rod is sleeved with an annular blade for cutting to separate the first piston and the annular sealing gasket.

The fit-connection between a free end of the fixed push rod and a blind hole at the center of an outer bottom surface of the first piston is a threaded connection.

The inner needle and the outer needle are integrated double-ended needle.

A pull tab is disposed at the center of the seal cap corresponding to an outer bottom surface of the first piston.

The second piston partitions the inner space of the vial body into an upper chamber and a lower chamber.

(1.3) A reversely pressed medicinal xiding vial, characterized in that it includes a vial body whose inner wall is a straight cylinder, a first piston is disposed on a position close to the vial opening of the vial body, a blind hole is disposed at the center of an outer bottom surface of the first piston, the vial opening is provided with an outer edge, and a seal cap is fixed on the out edge to prevent the first piston from falling off.

The further improvement of the above technical solution lies in:

an annular sealing gasket that is integrated therewith is disposed at an outer bottom surface of the first piston, the annular sealing gasket is positioned between the vial opening and the seal cap.

The center of the inner bottom surface of the first piston is disposed to be recessed.

The seal cap is an aluminum cap or a plastic cap.

A pull tab is disposed at the center of the seal cap corresponding to an outer bottom surface of the first piston.

(1.4) A reversely pressed medicinal xiding vial, characterized in that it includes a vial body whose inner wall is a straight cylinder, a first piston is disposed on a position close to the vial opening of the vial body, a blind hole is disposed at the center of an outer bottom surface of the first piston, the vial opening is provided with an outer edge, and a seal cap is fixed on the out edge to prevent the first piston from falling off; a second piston is provided in the middle t of the vial body a push plate is embedded in the second piston, and a needle guide hole is provided at the center of the push plate.

The further improvement of the above technical solution lies in:

an annular sealing gasket that is integrated therewith is disposed at an outer bottom surface of the first piston, the annular sealing gasket is positioned between the vial opening and the seal cap.

The center of the inner bottom surface of the first piston is disposed to be recessed.

The seal cap is an aluminum cap or a plastic cap.

A pull tab is disposed at an outer bottom surface of the first piston corresponding to the center of the seal cap.

The center of the second piston close to both sides of the push plate is disposed with trumpet ports having outward large ports, respectively.

The needle guide hole is formed by docking two trumpet ports having outward large ports.

The second piston partitions the inner space of the vial body into an upper chamber and a lower chamber.

(1.5) A reversely pressed dispensing apparatus includes a dispensing tube, a hollow needle positioned inside the dispensing tube is disposed at the bottom center of the dispensing tube; the hollow needle is composed of a head part and a rod part; the diameter of the head part of the hollow needle is less than the diameter of the rod part; and the head part of the hollow needle is provided with an inlet, and a side wall of the rod part is provided with an outlet.

The characteristics and the further improvement of the above technical solution lie in:

A guide sleeve is disposed inside the dispensing tube by clearance fit, and the rod part of the hollow needle slides to penetrate the guide sleeve.

The inlet of the head part of the hollow needle is disposed at a side wall of the head part thereof.

The dispensing tube is a tube-shaped frame.

(1.6) A reversely pressed injection apparatus, characterized in that it includes an injection tube, a fixed push rod and an inner needle longitudinally penetrating the fixed push rod are disposed at the bottom center of the injection tube inside the injection tube, a needle head of the inner needle sticks out of the fixed push rod, an outer needle is provided at an outlet port of the injection tube, and a tail part of the outer needle is connected with a tail part of the inner needle.

The characteristics and the further improvement of the above technical solution lie in:

The fixed push rod is slide-penetrated with a guide plate.

A free end of the fixed push rod is sleeved with an annular blade.

The outer needle is screw-connected with the outlet port of the injection tube.

The outlet port of the injection tube is provided with a protective cover for the outer needle; and the protective cover is a rubber cover or a plastic cover. The inlet of the inner needle is disposed at a side wall thereof.

The inner needle and the outer needle are integrated double-ended needle.

The injection tube is a tube-shaped frame.

The first group of technical solutions of the present disclosure possesses prominent substantive features and represents notable progress. The reversely pressed medicinal xiding vial includes a vial body whose inner wall is a straight cylinder, a first piston is disposed on a position close to the vial opening of the vial body, a blind hole is disposed at the center of an outer bottom surface of the first piston, the vial opening is provided with an outer edge, and a seal cap is fixed on the out edge to prevent the first piston from falling off; and an annular sealing gasket that is integrated therewith is disposed at an outer bottom surface of the first piston, the annular sealing gasket is positioned between the vial opening and the seal cap. The first piston first encapsulates a medicine, the annular sealing gasket secondarily encapsulates a medicine and the cap thirdly encapsulates a medicine; and the three encapsulations may adopt traditional processes, whose preparations are easy, and which may easily realize terminal sterilization.

The reversely pressed injection apparatus thereof includes an injection tube, a fixed push rod and an inner needle longitudinally penetrating the fixed push rod are disposed at the bottom center of the injection tube inside the injection tube, a needle head of the inner needle sticks out of the fixed push rod, an outer needle is disposed at an outlet port of the injection tube, and a tail part of the outer needle is commu- nicated with a tail part of the inner needle. A free end of the fixed push rod is sleeved with an annular blade for cutting to separate the first piston and the annular sealing gasket during the injection. The medicine has a small probability of contacting the externalities. When the inner needle and the outer needle are integrated double-ended needle, the medicine is thoroughly insulated from the externalities during the injection, which better solves the problem of secondary pollution during injecting a medicine.

The above structural characteristics of the first group of technical solutions of the present disclosure contribute to revolutionary improvements on medicinal liquid: (1) The medicinal liquid filled by a pharmaceutical factory may be directly injected into a body. (2) The water aqua filled by a pharmaceutical factory may be used to surgically wash a wound. (3) When powder filled in a cillin vial and water aqua filled in a reversely pressed medicinal xiding vial with a single chamber are dispensed, the water powder medicinal solution may be inversely sucked into the vial body by means of the reversely pressed injection apparatus using a reversely pressed principle and then injected into a human body; and the dispensing process is free from pollution. (4) When powder filled in a reversely pressed medicinal xiding vial with a single chamber and water aqua filled in a reversely pressed xiding vial of a single chamber are dispensed, likewise, the dispensing process is free from pollution. (5) For a reversely pressed medicinal xiding vial powder with double chambers, the dispensing process thereof is instant performed, and preparation and injection thereof are even more free from pollution. (6) The reversely pressed medicinal xiding vial may be directly applied to an automatic injection pen. (7) The reversely pressed medicinal xiding vial may be directly applied to an automatic pump for large volume infusion. These revolutionary improvements do not need to use a general needle tube or require the dispensing in a bacteria-free environment, and allow a medicine to be directly injected into a human body to reduce secondary pollution; the improvements make the dispensing easy and solve the problem of secondary pollution during the injection, which realize seamless connection among medicine manufacture, sale, dispensing and injection of human body and proposes a brand new concept that is fully enclosed, instant dispensing, pollution free and large bacteria-free.

2. Another one of the purposes of the present disclosure lies in providing an assembly of a general medicinal xiding vial and a general injection apparatus, which can ensure the sealing reliability and terminal sterilization of a general medicinal xiding vial, conveniently dispense and solve the problem of secondary pollution during the injection.

In order to achieve the above purpose, the following second group of technical solutions is adopted by the present disclosure.

(2.1) An assembly of a general medicinal xiding vial and a general injection apparatus, characterized in that it includes a general medicinal xiding vial and a general injection apparatus;

the general medicinal xiding vial includes a vial body whose inner wall is a straight cylinder, a first piston is disposed close to the vial opening of the vial body and a push plate is clad in the first piston, and a needle guide hole is provided at the center of the push plate; The vial opening is provided with a rubber plug and a cap for sealing;

the general injection apparatus includes an injection tube, an inner needle is disposed at the bottom of the injection tube inside the injection tube, and a sleeve needle is disposed outside the inner needle; the diameter of the sleeve needle is larger than the diameter of the needle guide hole; a needle head of the inner needle sticks out of the sleeve needle, a tail part of the inner needle is connected with an outlet of the injection tube, and an outer needle is disposed at the outlet of the injection tube; and an inner wall of the injection tube clearance-fits an outer edge of the vial opening.

The characteristics and the further improvement of the above technical solution lie in:

In the general medicinal xiding vial, the inner wall of the vial body is a straight cylinder which fits the first piston. In the general medicinal xiding vial, the first piston is made of a medicinal rubber material.

In the general medicinal xiding vial, the centers of two sides of the first piston close to the push plate are disposed with trumpet ports having outward large ports, respectively.

In the general medicinal xiding vial, the needle guide hole is formed by docking two trumpet ports having outward large ports.

In the general medicinal xiding vial, the seal cap is an aluminum cap or a plastic cap.

In the general injection apparatus, the inner needle and the sleeve needle are clearance-fitted, and both sides of the sleeve needle are provided with ventilation gaps, respectively, or ventilation holes are disposed close to both sides thereof, respectively.

In the general injection apparatus, the inner needle and the outer needle are integrated double-ended needle.

In the general injection apparatus, a guide sleeve is disposed inside the injection tube by clearance fit, the sleeve needle slides to penetrate the guide sleeve, and the guide sleeve hoops an outer edge of the vial opening.

In the general injection apparatus, the injection tube is a tube-shaped frame.

(2.2) A general medicinal xiding vial, characterized in that it includes a straight vial body, a first piston is disposed close to the vial opening of the vial body and a push plate is embedded in the first piston, and a needle guide hole is disposed at the center of the push plate; and the vial opening is provided with a rubber plug and a seal cap for sealing.

The characteristics and the further improvement of the above technical solution lie in:

The inner wall of the vial body is a straight cylinder which fits the first piston.

The first piston is made of a medicinal rubber material.

The centers of two sides of the first piston close to the push plate are formed as trumpet ports having outward large ports, respectively.

The needle guide hole is formed by docking two trumpet ports having outward large ports.

The cap is an aluminum cap or a plastic cap.

(2.3) A general injection apparatus, characterized in that it includes an injection tube, an inner needle is disposed at the bottom of the injection tube inside the injection tube, and a sleeve needle is disposed outside the inner needle; a needle head of the inner needle sticks out of the sleeve needle, a tail part of the inner needle is connected with an outlet of the injection tube, and an outer needle is disposed at the outlet of the injection tube; and an inner wall of the injection tube clearance-fits an outer edge of the vial opening.

The characteristics and the further improvement of the above technical solution lie in:

The inner needle and the sleeve needle are clearance-fitted, and both sides of the sleeve needle are provided with ventilation gaps, respectively, or ventilation holes are provided close to both sides thereof, respectively.

The inner needle and the outer needle are integrated double-ended needle.

A guide sleeve is disposed inside the injection tube by clearance fit, the sleeve needle penetrate the guide sleeve which is slidable along the sleeve needle, and the guide sleeve hoops an outer edge of the vial opening.

The injection tube is a tube-shaped frame.

An assembly of a general medicinal xiding vial and a general injection apparatus of the present disclosure includes a general medicinal xiding vial and a general injection apparatus. Wherein the general medicinal xiding vial includes a vial body whose inner wall is a straight cylinder, a first piston is disposed close to the vial opening of the vial body and clad with a push plate therein, and a needle guide hole is disposed at the center of the push plate; the vial opening is provided with a rubber plug and a seal cap for sealing; the first piston first encapsulates a medicine and the rubber plug and the cap secondarily encapsulate a medicine, hence, the sealing thereof is reliable, and the two encapsulations may adopt traditional technologies, it is terminal sterilized and easily prepared; also, the injection function is realized by pushing the first piston during the use.

The general injection apparatus thereof includes an injection tube, an inner needle is disposed at the bottom of the injection tube inside the injection tube, and a sleeve needle is disposed outside the inner needle; the diameter of the sleeve needle is larger than the diameter of the needle guide hole; a needle head of the inner needle sticks out of the sleeve needle, a tail part of the inner needle is connected with an outlet of the injection tube, and an outer needle is disposed at the outlet of the injection tube; and an inner wall of the injection tube clearance-fits an outer edge of the vial opening. The seal cap of the general medicinal xiding vial is first opened during the use, the outer edge of the vial opening slides along the inner wall of the injection tube, the inner needle and the sleeve needle impale the rubber plug, respectively, the inner needle further impales the first piston and contacts the medicine via the needle guide hole with the pushing of the vial body, while the sleeve needle pushes the first piston, the medicine is discharged through the inner needle and the outer needle, thereby realizing the injection of the medicine. As such, the medicine has a smaller probability of contacting the externalities during the injection. When the inner needle and the outer needle are integrated double-ended needle, the medicine is thoroughly insulated from the externalities during the injection, which better solves the problem of secondary pollution during injecting a medicine.

The second group of technical solutions of the present disclosure has the following notable structural characteristics as compared with a traditional general medicinal xiding vial and a traditional general injection apparatus: (1) The inner wall of the vial body is a straight cylinder which is matching with the first piston, which is single-directional opened, so as to be different from the double-directional opening of the card vial. (2) The first piston is clad with a push plate therein, which may be impaled by the inner needle for water passing and different from a general piston. (3) There is a needle guide hole at the middle of the push plate, the diameter of the inner needle is smaller than the diameter of the needle guide hole for the inner needle to easily impale the first piston; and the diameter of the needle guide hole is smaller than the diameter of the sleeve needle to prevent the sleeve needle from passing through, such that the push plate functions to push the first piston forward. (4) The inner needle is longer than the sleeve needle, and the longer part is larger than the thickness of the first piston to ensure the inner needle to contact the medicinal liquid. (5) The injection tube may be designed with a handle for easy operation and use. The bottom of the injection tube is provided with an air hole for pushing the vial body into the injection tube. (6) A positioning sleeve is a slideable positioning sleeve. The above structural characteristics of the present disclosure contribute to revolutionary improvements on the filling and injection of the medicinal vial: (1) The filled medicinal liquid may be directly injected into a body. (2) The filled water may be used to surgically wash a wound. (3) When a cillin vial powder is dispensed, the water powder medicinal solution may be inversely sucked into the vial body using a reversely pressed principle and then injected into a human body. These revolutionary improvements do not need to use a general needle tube or require the dispensing in a bacteria-free environment, and allow a medicine to be directly injected into a human body to reduce secondary pollution.

BRIEF DESCRIPTION OF THE DRAWINGS

Below the embodiments are described in detail in conjunction with the accompanying drawings to further explain the present disclosure.

Wherein 1. vial body; 2. first piston; 3. blind hole; 4. annular sealing gasket; 5. seal cap; 6. pull tab; 7. second piston; 8. push plate; 9. dispensing tube; 10. hollow needle; 1001. inlet; 1002. outlet; 11. guide sleeve; 12. injection tube; 13. fixed push rod; 14. inner needle; 15. outer needle; 16. guide plate; 17. annular blade; 18. protective cover; 19. rubber plug; 20. medicine; 21. sleeve needle.

DETAILED DESCRIPTION OF EXEMPLARY EMBODIMENTS

Below the detailed embodiments are described in detail in conjunction with FIGS. 1-14 to further explain the first group of technical solutions of the present disclosure.

Figures 1, 2, 3:
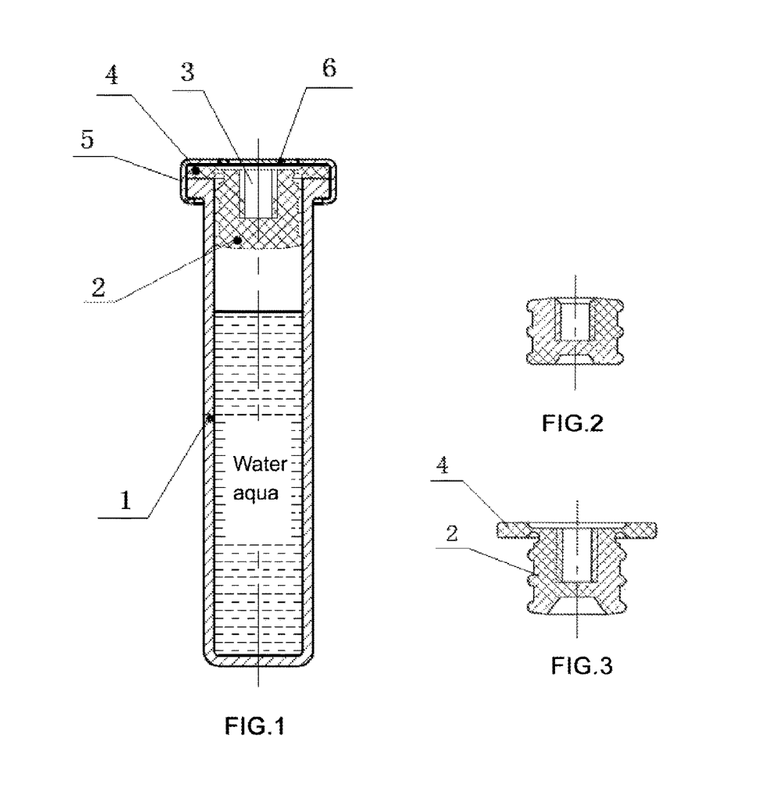
FIG. 1 is a schematic view of the structure of a reversely pressed medicinal xiding vial with a single chamber of the present disclosure.
FIG. 2 is a schematic view of one structure of a first piston of a reversely pressed medicinal xiding vial with a single chamber of the present disclosure.
FIG. 3 is a schematic view of the another structure of the first piston of a reversely pressed medicinal xiding vial with a single chamber of the present disclosure.

Referring to FIG. 1, a reversely pressed medicinal xiding vial with a single chamber of the present disclosure is shown, briefly named as a reversely pressed xiding vial with a single chamber, whose vial body 1 is a straight cylinder. A first piston 2 is disposed on a position close to the vial opening of the vial body 1, a blind hole 3 is disposed at the center of an outer bottom surface of the first piston 2, the vial opening is provided with an outer edge, and a seal cap 5, which may be an aluminum cap or a plastic cap, is fixed on the out edge to prevent the first piston 2 from falling off. A pull tab 6 is disposed at the center of the seal cap 5 corresponding to an outer bottom surface of the first piston 2, so as to easily opening the seal cap for injection.

In the present embodiment, an annular sealing gasket 4 that is integrated therewith is disposed at an outer bottom surface of the first piston 2 in order to ensure the sealing, and the annular sealing gasket 4 is positioned between the outer edge of the vial opening and the seal cap 5. Meanwhile, the center of the inner bottom surface of the first piston 2 is disposed to be recessed, as shown in FIGS. 2 and 3, in order to collect medicinal liquid during the later injection.

Figure 4:
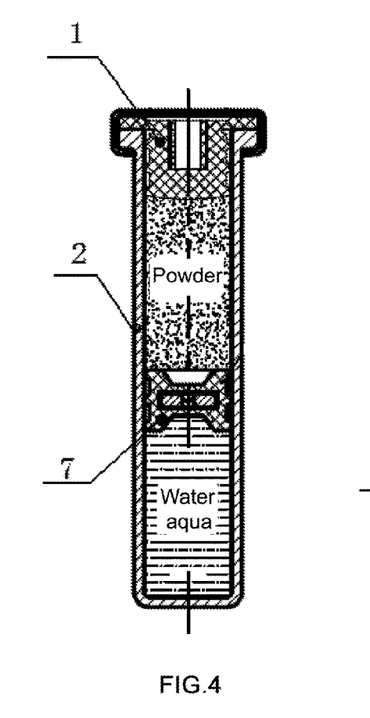
FIG. 4 is a schematic view of the structure of a reversely pressed medicinal xiding vial with double chambers of the present disclosure.
Figure 5:
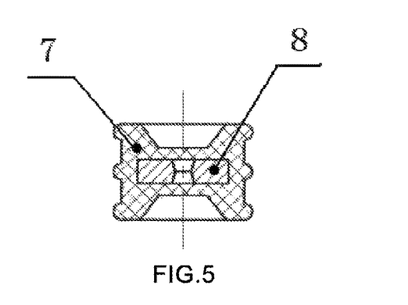
FIG. 5 is a schematic view of the structure of a second piston of a reversely pressed medicinal xiding vial with double chambers of the present disclosure.

Referring to FIG. 4, another reversely pressed medicinal xiding vial with double chambers of the present disclosure is shown, which is briefly named as a reversely pressed xiding vial with double chambers. It is different from the reversely pressed xiding vial with a single chamber in: a second piston 7 is disposed in the middle of the vial body, which partitions the inner space of the vial body into an upper chamber for medicine storage and a lower chamber for water aqua. As shown in FIG. 5, the second piston 7 has a push plate 8 clad therein. The center of the push plate 8 is provided with a needle guide hole, and the needle guide hole is formed by docking two trumpet ports with large ports toward outside, for easily puncturing; The centers of two side of the second piston 7 close to the push plate 8 are formed as trumpet ports with large ports toward outside, respectively, for collecting medicinal liquid during later injection.

Figure 6:
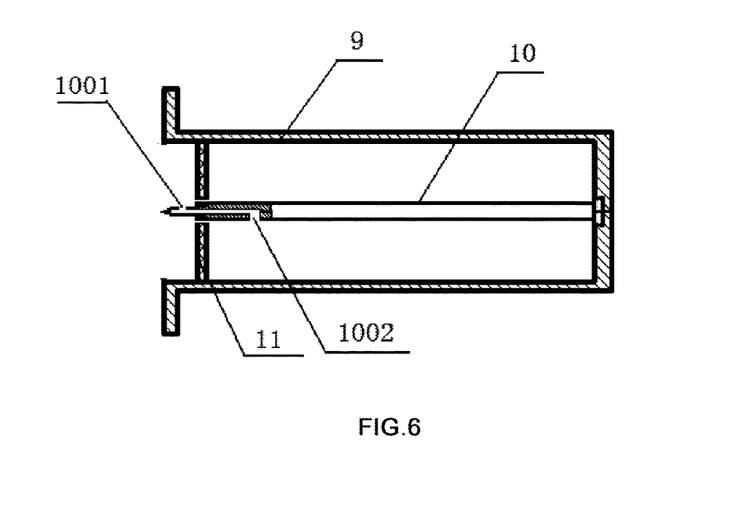
FIG. 6 is a schematic view of the structure of a reversely pressed dispensing apparatus of the present disclosure.

Referring to FIG. 6, a reversely pressed dispensing apparatus of the present disclosure is shown, whose function is to connect the upper chamber for medicine storage with the lower chamber for water aqua in the reversely pressed medicinal xiding vial with double chambers, and prepare a mixed medicinal liquid and forming a single chamber. In the reversely pressed dispensing apparatus, a hollow needle 10 is provided inside the dispensing tube 9 at the bottom center of the dispensing tube 9. The hollow needle 10 is composed of a head part and a rod part, and the diameter of the head part of the hollow needle 10 is smaller than the diameter of the rod part. An inlet 1001 is provided at a side wall of the head part of the hollow needle 10, and an outlet 1002 is provided at a side wall of the rod part. The dispensing tube 9 may be a tube-shaped frame to simplify the structure. A guide sleeve 11 is disposed inside the dispensing tube 9 through clearance fit, and the rod part of the hollow needle 10 penetrates the guide sleeve 11 and the guide sleeve 11 may slide along the hollow needle 10.

Figure 7:
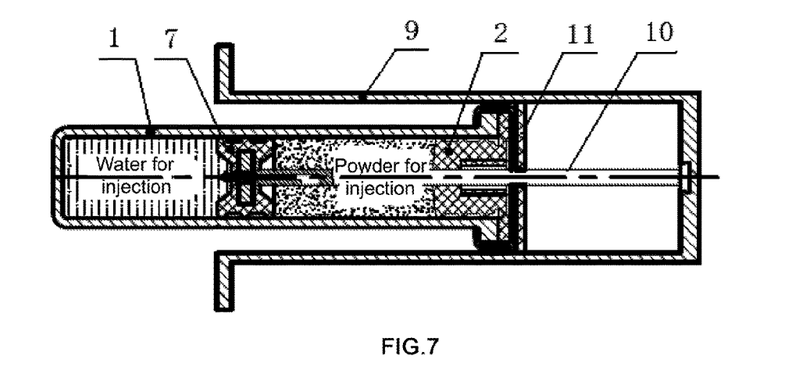
FIG. 7 is a dispensing use principle view of a reversely pressed dispensing apparatus and a reversely pressed medicinal xiding vial with double chambers of the present disclosure.

The principle for dispensing by using the reversely pressed dispensing apparatus and the reversely pressed medicinal xiding vial with double chambers of the present disclosure will be explained with reference to FIG. 7. In the reversely pressed medicinal xiding with double chambers, the second piston 7 thereof partitions the vial body into an upper chamber for reserving powder agentia and a lower chamber for reserving water aqua for injection. During dispensing, the vial opening of the reversely pressed medicinal xiding vial with double chambers is aligned with the center of the dispensing tube 9 of the reversely pressed dispensing apparatus, the vial opening attaches to the guide sleeve 11 to be directly or rotationally pushed into the dispensing tube 9, the hollow needle 10 penetrates the first piston 2 and then the head part of the hollow needle 10 passes through the second piston 7 and sticks into the lower chamber with water aqua, and the upper chamber for medicine storage and the lower chamber for water aqua are communicated through the inlet 1001 of the head part and the outlet 1002 of a side wall of the rod part of the hollow needle 10; at this moment, since the second piston 7 includes the push plate 8 therein and the center of the push plate 8 is provided with the needle guide hole, the diameter of the head part of the hollow needle 10 is smaller than the diameter of the needle guide hole, the diameter of the rod part is larger than the diameter of the guide needle, when the reversely pressed medicinal xiding vial with double chambers is continuously pushed, the rod part of the hollow needle 10 pushes the second piston 7 toward the vial bottom through pushing the push plate 8, the injection water in the lower chamber flows toward the upper chamber due to a reverse pressure until the second piston 7 moves to reach the vial bottom. The lower chamber for water aqua disappears, the injection water and the powder agentia mix and the volume of the upper chamber for medicine storage reaches the maximum. Finally, the reversely pressed dispensing apparatus is pulled out, and the reversely pressed medicinal xiding vial with double chambers becomes a reversely pressed medicinal xiding vial with a single chamber in form.

Figure 8:
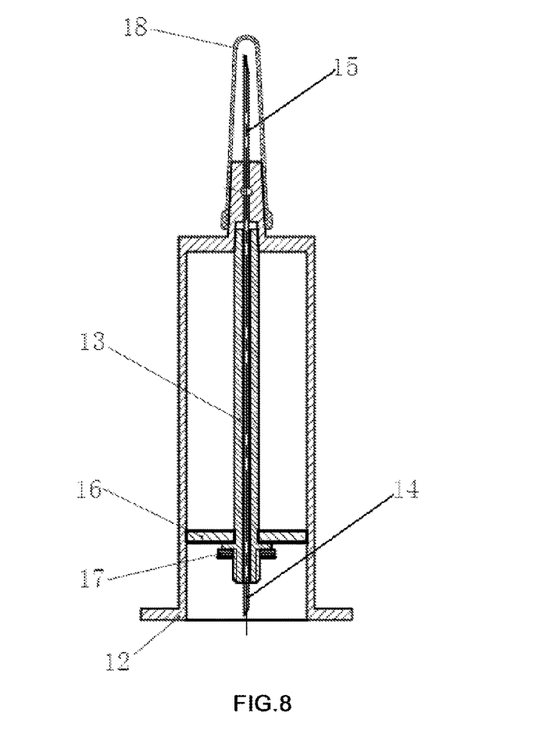
FIG. 8 is a schematic view of the structure of a reversely pressed injection apparatus of the present disclosure.

Referring to FIG. 8, a reversely pressed injection apparatus of the present disclosure is shown. The reversely pressed injection apparatus includes a injection tube 12, a fixed push rod 13 positioned inside the injection tube 12 and an inner needle 14 longitudinally penetrating the fixed push rod 13 are disposed at the bottom center of the injection tube 12, a needle head of the inner needle 14 extends out of the fixed push rod 13, an outer needle 15 is disposed at an outlet port of the injection tube 12, and a tail part of the outer needle 15 is connected with a tail part of the inner needle 14. The free end of the fixed push rod 13 is able to fit and connect with the blind hole 3 at the center of an outer bottom surface of the first piston 2 of the reversely pressed medicinal xiding vial, and the fit-connection may be a clamp connection or a threaded connection, and a threaded connection is selected in the present embodiment.

For engagement while using the reversely pressed medicinal xiding vial with a single chamber as shown in FIG. 1 and the reversely pressed medicinal xiding vial with double chambers as shown in FIG. 4, in the above reversely pressed medicinal xiding vial, an annular sealing gasket 4 integrated with the first piston 2 is disposed at an outer bottom surface of the first piston 2, and the annular sealing gasket 4 is positioned between the vial opening and the seal cap 5. In order to cut and separate the first piston 2 from the annular sealing gasket 4 during the use for injection, a free end of the fixed push rod 13 of the corresponding reversely pressed injection apparatus is sleeved with an annular blade 17. The blade edge of the annular blade 17 is in a wave shape for facilating rotationally cutting.

In addition, in the present embodiment, a guide plate 16 is provided on the fixed push rod 13, thorough which the fixed push rod 13 penetrates and along which the fixed push rod 13 is slidable, for guiding the reversely pressed medicinal xiding during the injection. An outer needle 15 is provided at the outlet port the outlet port of the injection tube 12 through a firmly reliable threaded connection. Alternatively, a technical solution of double-ended needles in which the inner needle 14 is integrated with the outer needle 15 may also be adopted. The outer needle 15 is protected by a protective sleeve 18 which may be a rubber sleeve or a plastic sleeve. The injection tube 12 may also be a tube-shaped frame to simplify the structure of the reversely pressed injection apparatus. The inlet of the inner needle 14 may be disposed at a side wall thereof to prevent from cutting off debris from the first piston while the inner needle 14 punctures through the first piston.

Figure 9:
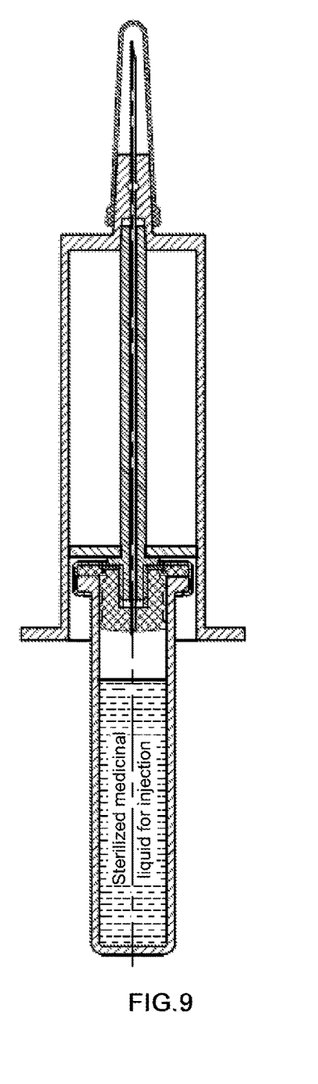
FIG. 9 is a schematic view showing a principle for injection by using a reversely pressed injection apparatus and a reversely pressed medicinal xiding vial with a single chamber of the present disclosure.

Referring to FIG. 9, a principle for rejection by using the reversely pressed injection apparatus and the reversely pressed medicinal xiding vial with a single chamber of the present disclosure is shown. During the use for injection, the seal cap of the reversely pressed medicinal xiding vial with a single chamber in which water aqua (sterile water for injection) is filled is first removed or the pull tab at the center of the seal cap is first pulled out, and then the vial opening aligns with the center of the injection tube of the reversely pressed injection apparatus, the vial opening attaches to the guide plate to be rotationally pushed, the inner needle first impales into the first piston, the free end of the fixed push rod of the reversely pressed injection apparatus is screwed into the blind hole disposed at the center of the outer bottom surface of the first piston, and meanwhile the annular blade sleeved at the free end of the fixed push rod gradually cuts to separate the first piston from the annular sealing gasket. When the first piston is separated from the annular sealing gasket, the inner needle impales into the first piston, and the free end of the fixed push rod is screwed into the bottom of the blind hole; the reversely pressed medicinal xiding vial with a single chamber is continuously rotationally or directly pushed, and the water aqua in the reversely pressed medicinal xiding vial with a single chamber is discharged through the inner needle and the outer needle under the function of reverse pressure, thereby realizing the injection function.

Figure 10:
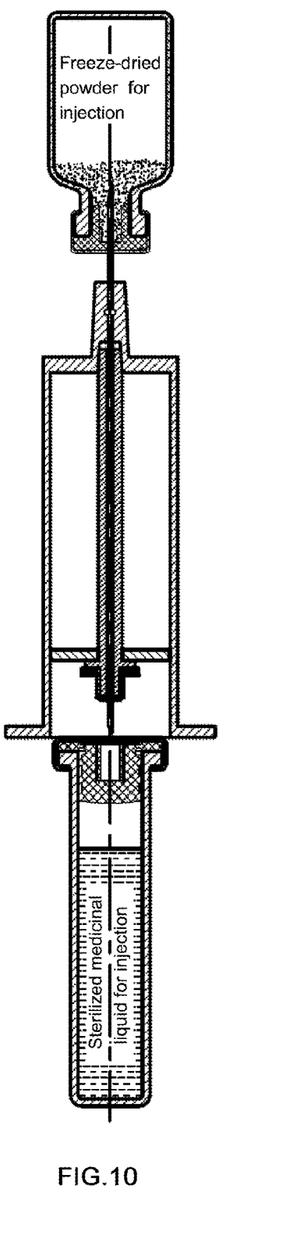
FIG. 10 is a schematic view for showing a dispensing initial process between a reversely pressed medicinal xiding vial with a single chamber and a cillin vial by using a reversely pressed injection apparatus of the present disclosure.
Figures 11, 12:
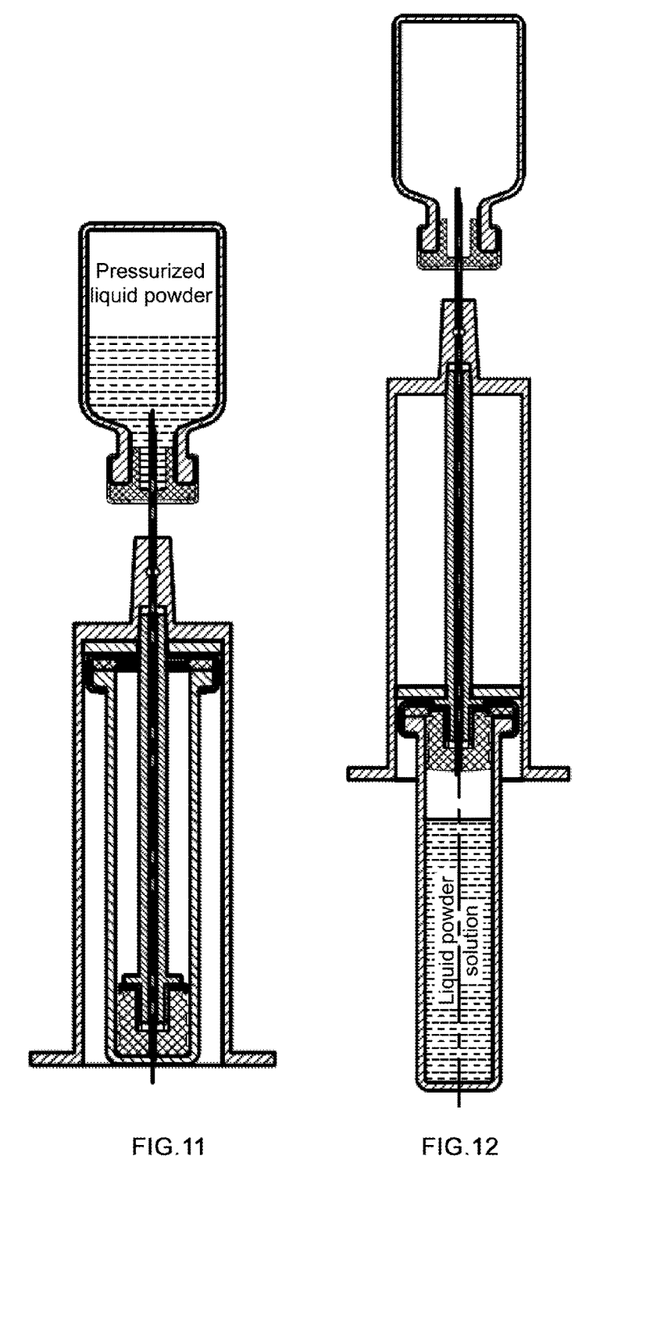
FIG. 11 is a schematic view for showing a dispensing mixing process between a reversely pressed medicinal xiding vial with a single chamber and a cillin vial by using a reversely pressed injection apparatus of the present disclosure.
FIG. 12 is a schematic view for showing a dispensing inversely sucking process between a reversely pressed medicinal xiding vial with a single chamber and a cillin vial by using a reversely pressed injection apparatus of the present disclosure.

Referring to FIGS. 10, 11 and 12, a dispensing process between the reversely pressed medicinal xiding vial with a single chamber and a cillin vial by using the reversely pressed injection apparatus is explained. Wherein powder (freeze-dried powder for injection) is filled in the cillin vial, and water aqua (sterile water for injection) is filled in the reversely pressed medicinal xiding with a single chamber.

During the initial dispensing process, the outer needle first impales into the cillin vial, and then the seal cap of the reversely pressed medicinal xiding vial with a single chamber in which water aqua (sterile water for injection) is filled is removed or the pull tab at the center of the seal cap is pulled out, the vial opening aligns with the center of the injection tube of the reversely pressed injection apparatus, the vial opening attaches to the guide plate to be rotationally pushed, the inner needle first impales into the first piston, the free end of the fixed push rod of the reversely pressed injection apparatus is screwed into the blind hole disposed at the center of the outer bottom surface of the first piston, and meanwhile the annular blade sleeved at the free end of the fixed push rod gradually cuts to separate the first piston with the annular sealing gasket. When the first piston is separated with the annular sealing gasket, the inner needle impales into the first piston, and the free end of the fixed push rod is screwed into the bottom of the blind hole.

The reversely pressed medicinal xiding vial with a single chamber is continuously rotationally or directly pushed, and the water aqua in the reversely pressed medicinal xiding vial with a single chamber is pressed into the cillin vial through the inner needle and the outer needle under the action of reverse pressure, and the water aqua is mixed with the powder, thereby realizing the dispensing mixing process.

After the dispensing mixing is completed, the cillin vial is filled with the pressurized liquid powder solution. At this moment, the reversely pressed medicinal xiding vial with a single chamber is loosen or drawn back, the pressurized liquid powder solution in the cillin vial is reversely sucked back to the reversely pressed medicinal xiding vial with a single chamber, and the dispensing reversely sucking process is completed.

Then, after the dispensing reversely sucking process is completed, the outer needle may be directly pulled out from the cillin vial and inserted into muscle or vein of human body to perform injection for human body using the reversely pressed injection apparatus and the reversely pressed medicinal xiding vial with a single chamber.

Figure 13:
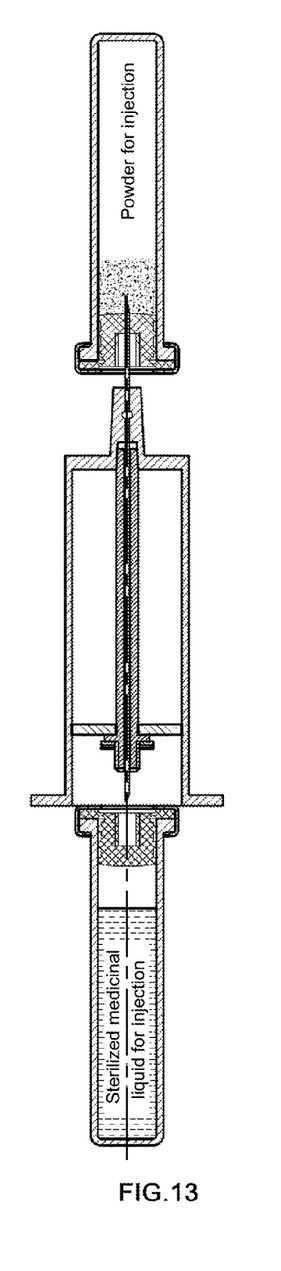
FIG. 13 is a schematic view for showing a dispensing process between two reversely pressed medicinal xiding vials with a single chamber by using a reversely pressed injection apparatus of the present disclosure.

Referring to FIG. 13, a dispensing process performed between two reversely pressed medicinal xiding vials with a single chambers by using a reversely pressed injection apparatus will be described. Wherein water aqua (sterile water for injection) is filled in one of the two reversely pressed medicinal xiding with a single chamber, and powder (powder for injection) is filled in the other reversely pressed medicinal xiding vial with a single chamber.

In comparison with above dispensing process between the reversely pressed medicinal xiding vial with a single chamber and the cillin vial by using the reversely pressed injection apparatus, the difference lies in that the cillin vial is replaced by the reversely pressed medicinal xiding vial with a single chamber in which powder is filled, and other steps are same substantively.

Figure 14:
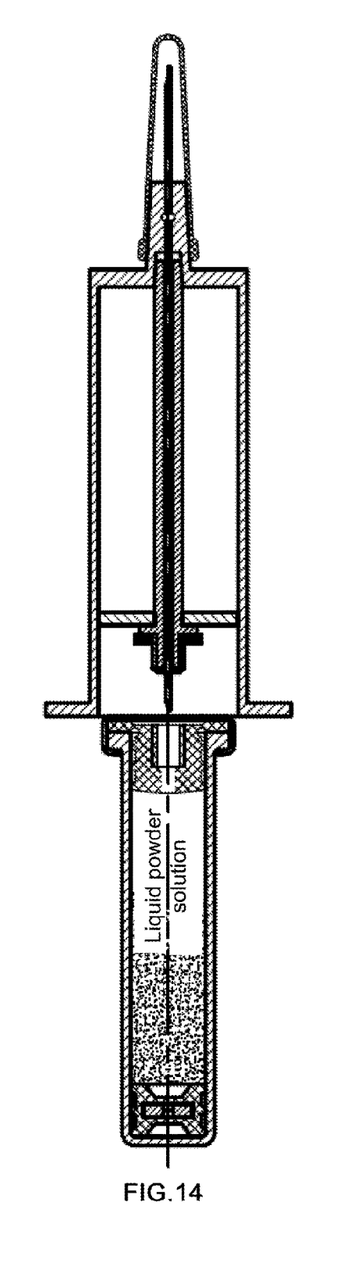
FIG. 14 is a schematic view for showing a injection process by using a reversely pressed injection apparatus and a reversely pressed medicinal xiding vial with double chambers in which the dispensing is completed.

Referring to FIG. 14, the use principle of using a reversely injection apparatus and a reversely pressed medicinal xiding vial with double chambers for which the dispensing has been completed, for injection will be described. Wherein the reversely pressed medicinal xiding vial with double chambers for which the dispensing has been completed, becomes a reversely pressed medicinal xiding vial with a single chamber in principle, and the steps for injection thereof are the same as the steps for injection of the reversely pressed medicinal xiding vial with a single chamber.

Table 1 shows effect comparisons among the reversely pressed medicinal xiding vial of the first group of technical solutions of the present disclosure and the traditional medicinal vials. The medicinal xiding vial successfully solves the problem of secondary pollution during medicine dispensing and injection, which is applicable to a city hospital, and is also widely applicable to a place with poor sanitary conditions such as a mountain area or a countryside, and is further applicable to an open country, a ship, a battlefield, and a disaster area.

TABLE 1

|  | Traditional Manufacture | Traditional Dispensing | Direct Injection | Automatic Injection Pen | Infusion Pump |
| --- | --- | --- | --- | --- | --- |
| Ampoule Vial | Terminal Sterilization | Possible Pollution | Possible Pollution | Not Applicable | Not Applicable |
| Cillin Vial | Terminal Sterilization | Possible Pollution | Possible Pollution | Not Applicable | Not Applicable |
| Card Vial | Non-terminal Sterilization | No Pollution | No Pollution | Applicable | Applicable |
| Prefilled Injector | Non-terminal Sterilization | No Pollution | No Pollution | Not Applicable | Not Applicable |
| Reversely Pressed Xiding Vial | Terminal Sterilization | No Pollution | No Pollution | Applicable | Applicable |

Below the detailed embodiments are described in detail with reference to FIGS. 15-17 to further explain the second group of technical solutions of the present disclosure.

Figure 15:
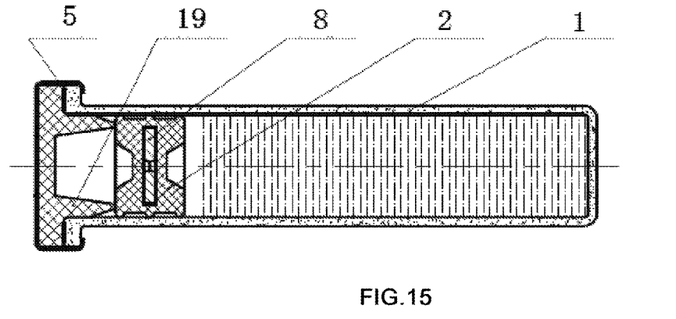
FIG. 15 is a schematic view of the structure of a general medicinal xiding vial of the present disclosure.

Referring to FIG. 15, a general medicinal xiding vial of the present disclosure is shown, mainly including a vial body 1 whose inner wall is a straight cylinder and a vial opening with an outer edge. The vial opening is disposed with a rubber plug 19 and a seal cap 5 for sealing. A first piston 2 is disposed close to the vial opening of the vial body 1, and the first piston 2 is made of a medicinal rubber material and is clad with a push plate 8 therein. A needle guide hole is disposed at the center of the push plate 8. The center of the first piston 2 close to both sides of the push plate 8 is disposed with trumpet ports having outward large ports, respectively. The trumpet port close to the outer side of the push plate 8 may faciliate a guide needle to impale, and the trumpet port close to the inner side of the push plate 8 may faciliate the complete sucking of a medicine. The needle guide hole is formed by connecting two trumpet ports having outward large ports.

It is to be explained that the outer cap disposed at the vial opening of the general medicinal xiding vial of the present disclosure is not limited to an aluminum cap and may also be a plastic cap.

Figure 16:
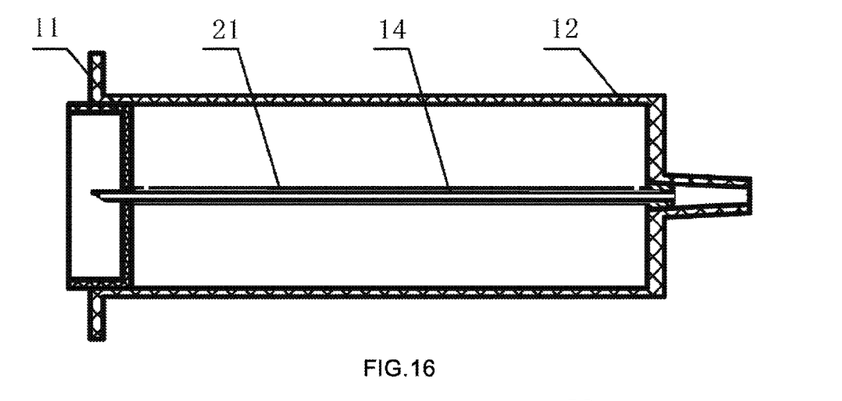
FIG. 16 is a schematic view of the structure of a general injection apparatus of the present disclosure.
Figure 17:
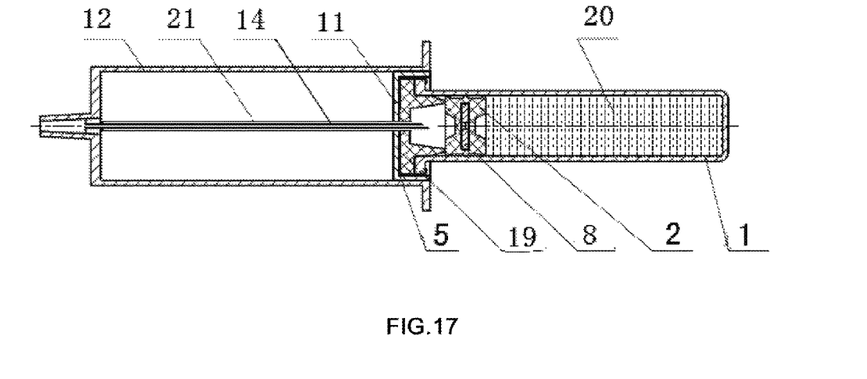
FIG. 17 is a schematic view of the fitting structure of a general medicinal xiding vial in FIG. 15 and a general injection apparatus of the present disclosure.

Referring to FIGS. 16 and 17, a fitting structure of a general injection apparatus and a general medicinal xiding vial will be explained. The general injection apparatus includes an injection tube 12 which may also be a tube-shaped frame. The injection tube 12 is adopted in the present embodiment, an inner needle 14 is provided inside the injection tube 12 at the bottom of the injection tube 12, a sleeve needle 21 is disposed outside the inner needle 14; and the functions of the inner needle 14 and the sleeve needle 21 are impaling the rubber plug, respectively. When the vial body 1 is pushed, the inner needle 14 impales the first piston 2 again and contacts the medicine 20 via the needle guide hole, while the sleeve needle 21 relies against the outer side of the push plate to push the first piston 2, and the medicine is discharged through the inner needle 14. Therefore, the diameter of the sleeve needle 21 is required to be larger than the diameter of the needle guide hole at the first piston 2, and the diameter of the inner needle 14 is surely smaller than the diameter of the needle guide hole; also, the needle head of the inner needle 14 is required to stick out of the sleeve needle 21 and can impale the first piston 2 through the needle guide hole to contact the medicine 20.

A tail part of the inner needle 14 is connected with an outlet of the injection tube 12, and an outer needle junction is disposed at the outlet of the injection tube 12 where an outer needle may be installed (not shown in figures). Another preferred solution is that the inner needle and the outer needle are formed as an integrated double-ended needle. When the inner needle 14 and the outer needle are integrated double-ended needle, the medicine is thoroughly insulated from the externalities during the injection, which better solves the problem of secondary pollution during injecting a medicine.

In the present embodiment, a guide sleeve 11 is disposed inside the injection tube 12 through a clearance fit. The sleeve needle 21 penetrates and slide along the guide sleeve 11. The guide sleeve 11 hoops an outer edge of the vial opening. The injection tube 12 clearance-fits the guide sleeve 11, such that the vial body may be easily pushed into the injection tube 12. In an alternative solution, they may also be slide fit, and it is necessary to provide a vent hole at the bottom of the injection tube 12. Obviously, the problem for air venting does not exist when the injection tube 12 is a tube-shaped frame.

That the inner needle 14 and the sleeve needle 21 may be clearance-fitted therebetween, and both sides of the sleeve needle are disposed with vent gaps, respectively, or ventilation holes are disposed close to both sides thereof, respectively, which help to air exhaust and push the first piston during the use.

During the use, the seal cap is first opened, the outer edge of the vial opening is hooped within the guide sleeve 11, the vial body 1 slides along the inner wall of the injection tube 12, the inner needle 14 and the sleeve needle 21 impale the rubber plug 19, respectively. The inner needle further impales the first piston 2 and contacts the medicine 20 via the needle guide hole with continuously pushing the vial body 1, while the sleeve needle 21 relies against the push plate 8 and pushes the first piston 2. The medicine 20 is discharged through the inner needle 14 and the outer needle, thereby realizing the injection of the medicine. As such, the medicine has a smaller probability of contacting the externalities during the injection. When the inner needle 14 and the outer needle are integrated double-ended needle, the medicine is thoroughly insulated from the externalities during the injection, which better solves the problem of secondary pollution during injecting a medicine.

In addition, the general medicinal xiding vial of the present embodiment is not limited to filling liquid medicine and may also be used for filing powder. When a solvent is filling and after powder is dissolved, the above injection method of the above liquid medicine may be referred to. It is especially to be explained that when the general medicinal xiding vial of the present embodiment is filled with a solvent and the cillin vial is filled with powder, it can also be realized that the solvent and the powder do not contact the externalities, which prevents the problem of secondary pollution during the dispensing. The particular operations are as follows: inserting the outer needle into the cillin vial and inserting the inner needle into the xiding vial by using the general injection apparatus of the present embodiment, pushing the vial body of the xiding vial, the solvent is injected into the cillin vial to mix and dissolve the powder, loosing the vial body of the xiding vial, the liquid powder medicinal solution is automatically reversely sucked into the vial body of the xiding vial under the function of reverse pressure, and when the pressures of the general medicinal xiding vial and the cillin vial of the present embodiment achieves a balance, pulling the inner outer needle out, the outer needle does not suck ambient air and then may be directly injected into a human body. Therefore, the dispensing and injection thereof using the general medicinal xiding vial and the general injection apparatus of the present embodiment do not need a bacteria-free environment to be performed; in other words, using the general medicinal xiding vial and the general injection apparatus of the present embodiment can allow grass-root or countryside hospitals not to set up standard dispensing rooms.

Even if the embodiments of the present disclosure are described in conjunction with the accompanying drawings as above, but the present disclosure is not limited to the above detailed embodiments which are only illustrative and instructive instead of limiting. Many various forms may be further made by those ordinary skilled in the art may further under the inspiration of the present description without departing from the scope claimed by the claims the disclosure, which are all protected by the present disclosure.

The invention claimed is:

1. An assembly of a reversely pressed medicinal vial and a reversely pressed injection apparatus, comprising the reversely pressed medicinal vial and the reversely pressed injection apparatus, wherein the reversely pressed medicinal vial includes a vial body whose inner wall is a straight cylinder, a first piston is disposed on a position close to a vial opening of the vial body, a blind hole is disposed at a center of an outer bottom surface of the first piston, and the vial opening is provided with an outer edge protruding radially outwardly from the vial opening and a seal cap is fixed on the outer edge to prevent the first piston from falling off;

wherein the reversely pressed injection apparatus includes an injection tube, a fixed push rod and an inner needle which longitudinally penetrates the fixed push rod are provided at a bottom center of the injection tube inside the injection tube, a needle head of the inner needle sticks out of the fixed push rod, an outer needle is provided at an outlet port of the injection tube, a tail part of the outer needle is communicated with a tail part of the inner needle, an inner wall of the injection tube is clearance-fitting with the outer edge of the vial opening, and a free end of the fixed push rod is fitted and connected with the blind hole at the center of the outer bottom surface of the first piston, wherein an annular sealing gasket that is integrated therewith is disposed at the outer bottom surface of the first piston and positioned between the vial opening and the seal cap; and wherein the free end of the fixed push rod is sleeved with an annular blade, and when the reversely pressed medicinal vial is assembled with the reversely pressed injection apparatus, the annular blade cuts and separates the first piston from the annular sealing gasket, the inner needle impales into the first piston, the first piston is pushed into the vial body in a direction away from the vial opening by the fixed push rod, and the annular sealing gasket is disposed at the vial opening.

2. The assembly of a reversely pressed medicinal vial and a reversely pressed injection apparatus of claim 1, wherein the fit-connection between the free end of the fixed push rod and the blind hole at the center of the outer bottom surface of the first piston is a threaded connection.

3. The assembly of a reversely pressed medicinal vial and a reversely pressed injection apparatus of claim 1, wherein the inner needle and the outer needle are integrated double-ended needle.

4. The assembly of a reversely pressed medicinal vial and a reversely pressed injection apparatus of claim 1, wherein a pull tab is disposed at a center of the seal cap corresponding to the outer bottom surface of the first piston.

5. A reversely pressed medicinal vial comprising a vial body whose inner wall is a straight cylinder and a first piston disposed on a position close to a vial opening of the vial body, a center of an outer bottom surface of the first piston is provided with a blind hole, the vial opening has an outer edge protruding radially outwardly from the vial opening, and a seal cap is fixed on the outer edge to prevent the first piston from falling off, wherein an annular sealing gasket is integrally formed at the outer bottom surface of the first piston and interposed between the vial opening and the seal cap, a connection portion between the annular sealing gasket and the first piston has a thickness less than that of the annular sealing gasket to be cut, wherein the annular sealing gasket has a configuration to be cut from the first piston, and wherein when the annular sealing gasket is separated from the first piston, the first piston slides into the vial body in a direction away from the vial opening and a through-hole is formed on the annular sealing gasket disposed at the vial opening.

6. The reversely pressed medicinal vial of claim 5, wherein a recess is provided in a center of an inner bottom surface of the first piston.

7. The reversely pressed medicinal vial of claim 5, wherein the seal cap is an aluminum cap or a plastic cap.

8. The reversely pressed medicinal vial of claim 5, wherein a pull tab is provided at a center of the seal cap corresponding to the outer bottom surface of the first piston.

9. An assembly of a reversely pressed injection apparatus and a reversely pressed medicinal vial, the reversely pressed medicinal vial comprising,
a vial body whose inner wall is a straight cylinder and a first piston disposed on a position close to a vial opening of the vial body;
a center of an outer bottom surface of the first piston provided with a blind hole;
the vial opening having an outer edge protruding radially outwardly from the vial opening; and
a seal cap fixed on the outer edge to prevent the first piston from falling off, and the reversely pressed injection apparatus comprising,
an injection tube;
a fixed push rod; and,
an inner needle which longitudinally penetrates the fixed push rod are disposed at a bottom center of the injection tube inside the injection tube, wherein a needle head of the inner needle sticks out of the fixed push rod, an outer needle is provided at an outlet port of the injection tube, and a tail part of the outer needle is communicated with a tail part of the inner needle, wherein an annular sealing gasket is integrally formed at the outer bottom surface of the first piston and interposed between the vial opening and the seal cap, wherein a free end of the fixed push rod is sleeved with an annular blade, and wherein when the reversely pressed medicinal vial is assembled with the reversely pressed injection apparatus, the annular blade cuts and separates the first piston from the annular sealing gasket, the inner needle impales into the first piston, the first piston is pushed into the vial body in a direction away from the vial opening by the fixed push rod, and the annular sealing gasket is disposed at the vial opening.

10. The reversely pressed injection apparatus of claim 9, wherein a guide plate is slidablely provided on the fixed push rod, with being penetrated by the fixed push rod.

11. The reversely pressed injection apparatus of claim 9, wherein the outer needle is thread-connected with the outlet port of the injection tube.

12. The reversely pressed injection apparatus of claim 9, wherein the outlet port of the injection tube is provided with a protective cover for the outer needle.

13. The reversely pressed injection apparatus of claim 12, wherein the protective cover is a rubber sleeve or a plastic sleeve.

14. The reversely pressed injection apparatus of claim 9, wherein an inlet of the inner needle is disposed at a side wall of the inner needle.

15. The reversely pressed injection apparatus of claim 9, wherein the inner needle and the outer needle are integrated double-ended needle.

16. The reversely pressed injection apparatus of claim 9, wherein the injection tube is a tube-shaped frame.

* * * * *